(12) United States Patent
Seki et al.

(10) Patent No.: US 7,868,192 B1
(45) Date of Patent: Jan. 11, 2011

(54) PROCESS FOR PRODUCING GLYCIDOL

(75) Inventors: Yuichiro Seki, Wakayama (JP); Tomoaki Sasa, Wakayama (JP); Hiroki Takeuchi, Wakayama (JP); Mitsuru Uno, Wakayama (JP); Masanori Namba, Wakayama (JP)

(73) Assignee: KAO Corporation, Tokyo (JP)

( * ) Notice: Subject to any disclaimer, the term of this patent is extended or adjusted under 35 U.S.C. 154(b) by 0 days.

(21) Appl. No.: 12/503,428

(22) Filed: Jul. 15, 2009

(51) Int. Cl.
*C07D 301/02* (2006.01)

(52) U.S. Cl. .................. 549/518; 549/229; 549/555

(58) Field of Classification Search .............. 549/518, 549/229, 555
See application file for complete search history.

(56) References Cited

U.S. PATENT DOCUMENTS 2,856,413 A * 10/1958 Malkemus et al. .......... 549/518

OTHER PUBLICATIONS

Mori et al., Chem. Commun., 2005, 3331-3333, May 27, 2005.*

* cited by examiner

*Primary Examiner*—Janet L Andres
*Assistant Examiner*—David E Gallis
(74) *Attorney, Agent, or Firm*—Birch, Stewart, Kolasch & Birch, LLP

(57) ABSTRACT

The present invention relates to a process for producing glycidol from glycerol carbonate by subjecting the glycerol carbonate to decarboxylation reaction in the presence of a solvent containing no active hydrogen. In the process, glycidol can be produced from glycerol carbonate as a raw material of the glycidol with a high selectivity.

6 Claims, No Drawings

PROCESS FOR PRODUCING GLYCIDOL

FIELD OF THE INVENTION

The present invention relates to a process for producing glycidol from glycerol carbonate.

BACKGROUND OF THE INVENTION

Glycidol is a useful substance as a raw material for polyglycerol, (poly) glycerol esters and dihydroxypropylamine as well as perfumes and cosmetics, detergents, drugs, paints, UV curing agents for semiconductors, etc.

As a method for producing glycidol compounds, there is known the method in which an aryl alcohol is oxidized in the presence of an oxidizing agent (for example, refer to JP 2001-106680A and JP 57-52341A). In addition, there is known the method in which glycerol carbonate is subjected to decarboxylation under a catalyst-free condition or in the presence of a neutral salt such as sodium sulfate (for example, refer to U.S. Pat. No. 2,856,413 and JP 6-157509A).

On the other hand, it is also known that the glycerol carbonate is produced by not only a method using phosgene but also a method of subjecting dimethyl carbonate, ethylene carbonate, propylene carbonate or the like and glycerol to exchange reaction therebetween, a method of obtaining the glycerol carbonate from glycerol and urea, etc.

Among these methods, the method using glycerol and urea is considered to be industrially advantageous, because it allows the glycerol carbonate to be produced in a facilitated manner at low costs. In this method, although the reaction proceeds even under a catalyst-free condition, it is known that the glycerol carbonate is produced from glycerol and urea with a high yield when using a Lewis acid such as zinc sulfate and manganese sulfate as a catalyst in the reaction (for example, refer to EP 0955298A). Further, it is also known the method in which glycerol and urea are reacted in the presence of a dehydration agent (for example, refer to JP 2000-247967A).

However, in these conventionally known methods, since the decarboxylation reaction of glycerol carbonate is carried out at a temperature as high as about 200° C., undesirable side reactions such as reaction between molecules of chemically unstable glycidol and reaction between glycidol and glycerol carbonate as a raw material of the glycidol tend to be induced to thereby cause problems such as low yield of glycidol as the aimed product.

Further, the conventionally known methods for producing glycidol from glycerol carbonate (for example, those methods as described in U.S. Pat. No. 2,856,413 and JP 6-157509A) have almost failed to certainly specify suppression of the side reactions. Thus, there are not conventionally known the methods for producing glycidol from glycerol carbonate by decarboxylation reaction of the glycerol carbonate which can achieve the technical task of producing the glycidol with a high selectivity while suppressing occurrence of the side reactions.

SUMMARY OF THE INVENTION

The present invention relates to a process for producing glycidol in which glycerol carbonate is subjected to decarboxylation reaction in the presence of a solvent containing no active hydrogen.

DETAILED DESCRIPTION OF THE INVENTION

The present invention relates to a process for producing glycidol from glycerol carbonate as a raw material with a high selectivity.

The present inventors have found that when subjecting glycerol carbonate to decarboxylation reaction in the presence of a solvent containing no active hydrogen, chemically unstable glycidol can be produced with a high selectivity.

Thus, the process for producing glycidol according to the present invention is characterized in that the glycidol is produced by subjecting glycerol carbonate to decarboxylation reaction in the presence of a solvent containing no active hydrogen.

(Production of Glycerol Carbonate)

The glycerol carbonate used as a raw material in the process of the present invention may be produced, for example, by such a reaction as shown in the following reaction formula in which glycerol represented by the following chemical formula (1) is reacted with urea represented by the following chemical formula (2) to obtain glycerol carbonate represented by the following chemical formula (3). When performing the reaction, it is preferred that the reaction system be previously dehydrated.

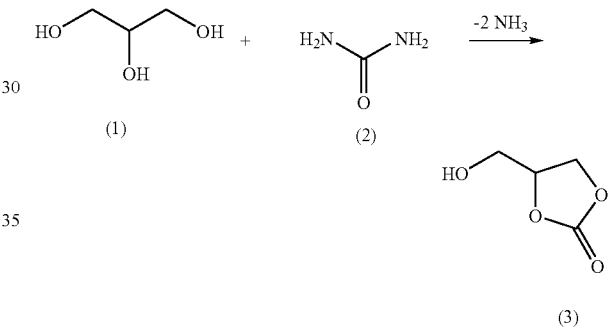

Although the reaction between glycerol and urea may proceed without using any catalyst, a Lewis acid catalyst, e.g., various sulfates such as zinc sulfate, manganese sulfate and magnesium sulfate, is preferably used in order to allow the reaction to smoothly proceed.

(Pretreatment Before Decarboxylation Reaction)

In the process of the present invention in which the thus obtained glycerol carbonate is subjected to decarboxylation reaction as described above, the raw glycerol carbonate may be subjected to purification treatment such as distillation as a pretreatment before the decarboxylation reaction, if required, but the glycerol carbonate may be directly subjected to decarboxylation reaction without such a purification treatment.

If the Lewis acid catalyst used for production of glycerol carbonate remains in the glycerol carbonate used in the decarboxylation reaction, selective production of glycidol therefrom tends to become difficult. Therefore, it is preferred that an amount of the residual Lewis acid catalyst in the glycerol carbonate be reduced.

The content of the Lewis acid catalyst in glycerol carbonate as the raw material is preferably 1500 ppm by mass or less, more preferably 1000 ppm by mass or less, even more preferably 500 ppm by mass or less and further even more preferably from 1 to 200 ppm by mass on the basis of the glycerol carbonate, from the viewpoint of high reaction yield of glycidol.

(Production of Glycidol)

As shown in the following reaction formula, glycerol carbonate represented by the chemical formula (3) is subjected to decarboxylation reaction in the presence of a solvent containing no active hydrogen to produce glycidol represented by the chemical formula (4).

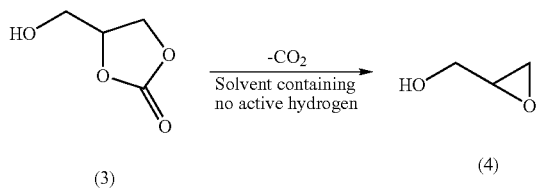

(Solvent Containing No Active Hydrogen)

The solvent containing no active hydrogen is used to reduce a concentration of the reaction system for the purpose of suppressing occurrence of undesirable side reactions such as reaction between molecules of the chemically unstable glycidol and reaction of glycidol with glycerol carbonate as a raw material of the glycidol. If a solvent containing an active hydrogen such as polyols is present in the decarboxylation reaction, the solvent tends to be reacted with glycerol carbonate or glycidol, which results in deterioration in yield of the glycidol. Therefore, it is preferred that no solvent containing an active hydrogen be used in the decarboxylation reaction, or the solvent containing an active hydrogen, if used therein, be present in a minimum amount. The boiling point of the solvent containing no active hydrogen as used in the present invention is preferably higher than a boiling point of glycidol, and more preferably higher by 10° C. or more, even more preferably higher by 20° C. or more, further even more preferably by 50° C. or more, than the boiling point of glycidol.

Examples of the solvent containing no active hydrogen include ether-based solvents; hydrocarbon-based solvents such as saturated hydrocarbon-based solvents, aromatic hydrocarbon-based solvents, halogen-containing hydrocarbon-based solvents and nitrogen-containing hydrocarbon-based solvents; amide-based solvents; and nitrile-based solvents. Among these solvents, from the viewpoint of completely avoiding occurrence of the reaction of the solvent with glycerol carbonate or glycidol, preferred are ether-based solvents, saturated hydrocarbon-based solvents and aromatic hydrocarbon-based solvents.

Examples of the ether-based solvents include diethylene glycol dimethyl ether, triethylene glycol dimethyl ether, tetraethylene glycol dimethyl ether and polyalkylene glycol dialkyl ethers.

Specific examples of the polyalkylene glycol dialkyl ethers include polymethylene glycol dimethyl ether, polymethylene glycol diethyl ether, polyethylene glycol dimethyl ether, polyethylene glycol diethyl ether, polypropylene glycol dimethyl ether and polypropylene glycol diethyl ether. The mass-average molecular weight of the polyalkylene glycol dialkyl ethers is not particularly limited, and is usually from 100 to 2000, preferably from 150 to 1500 and more preferably from 200 to 1000.

Examples of the saturated hydrocarbon-based solvents include saturated hydrocarbons having preferably 6 to 25 carbon atoms and more preferably 8 to 22 carbon atoms. Specific examples of the saturated hydrocarbon-based solvents include decane, dodecane, tetradecane, pentadecane, hexadecane, heptadecane, octadecane and nonadecane, as well as liquid paraffins. The liquid paraffins used as the solvent are not particularly limited as long as they are present in a liquid state at an ordinary temperature.

Examples of the aromatic hydrocarbon-based solvents include aromatic hydrocarbons having preferably 8 to 20 carbon atoms and more preferably 10 to 16 carbon atoms. Specific examples of the aromatic hydrocarbon-based solvents include phenyl alkanes such as 1-phenyl heptane and 1-phenyl octane, and naphthalene.

Among these solvents containing no active hydrogen, from the viewpoints of reducing a concentration of the reaction system and thereby suppressing occurrence of undesirable side reactions, preferred are ether-based solvents, as well as hydrocarbon-based solvents such as saturated hydrocarbon-based solvents and aromatic hydrocarbon-based solvents. Among these solvents, more preferred are polyalkylene glycol dimethyl ethers and liquid paraffins. More specifically, the polyalkylene glycol dimethyl ethers or liquid paraffins having a mass-average molecular weight of from 100 to 2000, preferably from 150 to 1500 and more preferably from 200 to 1000 are especially preferred.

These solvents may be used alone or in the form of a mixture of any two or more thereof.

When water is contained in the solvent containing no active hydrogen, there is such a risk that glycerol carbonate as the raw material and glycidol as the reaction product undergo hydrolysis. Therefore, it is preferred that the solvent used be previously purified by dehydration. The dehydration method is not particularly limited. For example, the solvent may be dehydrated and dried by an ordinary method using a drying agent such as metal hydrides.

The solvent containing no active hydrogen may be used in an amount of preferably from 1 to 500 parts by mass (g), more preferably from 10 to 400 parts by mass (g) and even more preferably from 20 to 300 parts by mass (g) on the basis of 100 parts by mass (g) of glycerol carbonate as the raw material. Meanwhile, for the reasons as described previously, it is more preferred that no solvent containing an active hydrogen be used, or the solvent containing an active hydrogen, if used, be present in a minimum amount. When using the solvent containing an active hydrogen, the solvent is used in an amount of preferably 10 parts by mass (g) or less and more preferably 5 parts by mass (g) or less on the basis of 100 parts by mass (g) of glycerol carbonate as the raw material. Even more preferably, substantially no solvent containing an active hydrogen is used in the reaction.

(Conditions of Decarboxylation Reaction)

The decarboxylation reaction of glycerol carbonate may be carried out without using any catalyst. However, the decarboxylation reaction is preferably carried out in the presence of a catalyst to allow the reaction to smoothly proceed. Examples of the suitable catalyst include neutral salts, e.g., alkali metal salts and/or alkali earth metal salts such as anhydrous sodium sulfate, sodium chloride and aluminosilicates (including A-type zeolites such as A3-type, A4-type and A5-type zeolites, Y-type zeolites, etc.). If weak acid salts such as zinc sulfate, manganese sulfate and sodium hydrogensulfate are used as the catalyst, the conversion rate of glycerol carbonate tends to be considerably deteriorated. Therefore, it is preferred that no weak acid salts be used in the decarboxylation reaction, or the weak acid salts, if used, be present in a minimum amount. Further, when basic salts such as sodium carbonate, sodium hydrogencarbonate and magnesium acetate are used as the catalyst, undesirable polymerization tends to occur in the reaction system, resulting in deterioration in yield of glycidol as aimed. Therefore, it is preferred that no basic salts be used in the decarboxylation reaction, or the basic salts, if used, be present in a minimum amount.

In order to avoid occurrence of undesirable side reactions such as reaction between molecules of chemically unstable glycidol and reaction between glycidol and glycerol carbonate as a raw material of the glycidol, glycerol carbonate is preferably dropped in the reaction system (hereinafter occasionally referred to as "dropping method"). The dropping rate of glycerol carbonate varies depending upon reaction temperature, reaction pressure, etc., and may be adjusted such that glycidol as produced is distilled out constantly and smoothly without remaining in the reaction system.

The decarboxylation reaction may be carried out not only by the dropping method but also by a batch method or a continuous method.

As the batch method, there may be used a batch reaction method in which glycerol carbonate and the catalyst are charged into a reaction vessel at the time of initiating the reaction, etc.

As the continuous method, there may be used a fixed bed reaction method in which glycerol carbonate is flowed through the catalyst packed and immobilized to allow the reaction of glycerol carbonate to proceed, a method in which a heterogeneous catalyst or a homogeneous catalyst is fed together with the raw material into a reactor, etc.

In the decarboxylation reaction, from the viewpoints of shortening a contact time with a heating source and suppressing occurrence of the side reactions while allowing the aimed reaction to proceed, and obtaining glycidol having a high purity, it is preferred that glycidol as produced be rapidly withdrawn from the reaction system. From the same viewpoints, the decarboxylation reaction is preferably conducted by a semi-batch method or a continuous method using a thin film reactor.

When using the thin film reactor, it is preferable to control a thickness of the thin film and renew a heat-transfer surface thereof. Further, it is also preferred that an inert gas such as nitrogen be introduced into the reactor, or the reaction be conducted under reduced pressure in order to promote separation of glycidol as produced.

As the thin film reactor, there may be used a stirring film type evaporator as described, for example, on page 406 of "Handbook of Chemical Engineering", (revised 5 edition, edited by The Society of Chemical Engineers, Japan, 1988), or a falling film distillation apparatus as described, for example, on page 493 of the same literature.

Further, there may also be used conventionally known reactors other than the above-mentioned reactors.

The method of forming the thin film in the thin film type reactor is not particularly limited, and there may be used any method capable of allowing a mixed liquid containing glycerol carbonate, the solvent containing no active hydrogen and, if required, the catalyst to pass over a heating surface in the form of a thin film. Examples of the method of forming the thin film include a falling method, an upward liquid film method, a wiper method, a stirring method, a rotating method and a centrifugal method.

The falling method means such a method in which the mixed liquid is allowed to naturally flow down along a heating inner wall surface of the reactor to form a thin film thereof. The upward liquid film method means such a method in which a film of liquid is pushed upwardly by a gas introduced from a bottom of the reactor to form a thin film thereof.

The wiper method means such a method in which the mixed liquid is allowed to naturally flow down along an inner wall surface of the reactor, and further wiped with a wiper blade to form a thin film thereof. The stirring method means such a method in which the mixed liquid fed to the reactor was stirred with a scraper, etc., to form a thin film thereof.

The rotating method means such a method in which the raw mixture is cast and flowed over a surface of a rotating disk to form a thin film thereof, or a thin film of the raw mixture is formed between an outer cylindrical tube and a rotating inner cylindrical tube. The centrifugal method means such a method in which a thin film is formed on both wall surfaces between outer and inner cylindrical tubes by a centrifugal force.

Among these methods, preferred are a falling method, a wiper method and a stirring method.

When the reaction is carried out by the dropping method or the batch method, an amount of the catalyst, e.g., neutral salts such as alkali metal salts and/or alkali earth metal salts, if used, is preferably from 0.01 to 10 mol, more preferably from 0.02 to 8 mol and even more preferably from 0.02 to 5 mol per 1 mol of glycerol carbonate.

The decarboxylation reaction is preferably carried out at a temperature of from 155 to 300° C., more preferably from 160 to 280° C. and even more preferably from 170 to 260° C. The reaction pressure is not particularly limited, and is preferably from 2.5 to 50 kPa and more preferably from 2.7 to 30 kPa.

The reaction time varies depending upon amounts of the raw material and solvent, reaction temperature, reaction pressure, etc., and is usually from 0.5 to 100 h and preferably from 1 to 10 h.

In addition, in order to efficiently distil glycidol as produced out of the reaction system, an inert gas such as nitrogen may be introduced into the liquid phase. The amount of the inert gas introduced varies depending upon reaction temperature, reaction pressure, etc., and may be adjusted such that the glycidol as produced is distilled out substantially constantly and smoothly without remaining in the reaction system.

EXAMPLES

In the following Examples and Comparative Examples, a gas chromatographic analysis was carried out under the following conditions.
"HP-6850 Series" available from Hewlett Packard Corp.
Column: "Agilent 19091 J-433E" ("HP-5"; 5% phenyl methyl siloxane; capillary: 30.0 m×250 μm×0.25 μm)
Inlet temperature: 270° C.; Detector temperature: 300° C.
Oven: 50° C. (2 min); 300° C. (10° C./min); 300° C. (5 min)

Production Example 1

Glycerol and urea which were accurately weighed in amounts of 301.1 g (3.27 mol) and 235.3 g (3.91 mol), respectively, were charged into a 1000 mL four-necked flask and then heated to 80° C. to prepare a uniform solution thereof. Thereafter, the resulting solution was subjected to dehydration treatment under reduced pressure.

Then, 20.7 g (0.13 mol) of zinc sulfate was charged into the flask, and the contents of the flask were heated 130° C. After heating, while blowing nitrogen into the obtained reaction solution, the pressure within the reaction system was maintained in the range of from 2.7 to 4.0 kPa under which the reaction was carried out for 10 h. After completion of the reaction, the pressure within the reaction system was returned to normal pressures under which the obtained reaction solution was allowed to stand for cooling to thereby obtain 401.9 g of a reaction product (purity of glycerol carbonate: 84%).

The thus obtained final reaction product was filtered to remove insoluble solids therefrom, and then subjected to thin film distillation at a temperature of 170° C. under a pressure of 0.4 kPa using a thin film distillation apparatus (type number: "2-03 Type" available from Shinko Pantech Co., Ltd.; heat-transfer area: 0.03 m$^2$), thereby obtaining 276.6 g of purified glycerol carbonate (purity of glycerol carbonate: 96%; glycerol content: 4%).

Example 1

Production of Glycidol

A 300 mL four-necked flask equipped with a fractionating column, a Liebig condenser and a nitrogen inlet pipe was charged with 20.0 g (0.14 mol) of anhydrous sodium sulfate and 100.3 g of polyethylene glycol dimethyl ether (PEG; available from Merck & Co., Inc.; average molecular weight: 500), and the contents of the flask were gradually heated to 200° C. under a pressure of 6.7 kPa. Also, the temperature of the fractionating column was maintained at 100° C. Thereafter, 210.3 g of glycerol carbonate produced in Production Example 1 were added dropwise into the flask over 4 h. After completion of the dropping, the resulting reaction mixture was aged under a pressure of 2.7 kPa for 2 h. During dropping of glycerol carbonate and aging of the reaction mixture after the dropping, nitrogen was introduced into the liquid phase at a rate of 50 mL/min. As a result of analyzing the obtained reaction product by gas chromatography, it was confirmed that the yield of glycidol was 101.5 g, and the selectivity to glycidol was 80%. In addition, it was confirmed that after completion of the reaction, no glycerol carbonate was present in the residue.

Example 2

A 300 mL four-necked flask equipped with a fractionating column, a Liebig condenser and a nitrogen inlet pipe was charged with 23.7 g (0.17 mol) of anhydrous sodium sulfate and 118.3 g of polyethylene glycol dimethyl ether (available from Merck & Co., Inc.; average molecular weight: 500), and the contents of the flask were gradually heated to 200° C. under a pressure of 6.7 kPa. Also, the temperature of the fractionating column was maintained at 100° C. Thereafter, 236.9 g (2.00 mol) of glycerol carbonate (available from Tokyo Chemical Industry Co., Ltd.) were added dropwise into the flask over 4 h. After completion of the dropping, the resulting reaction mixture was aged under a pressure of 2.7 kPa for 2 h. During dropping of glycerol carbonate and aging of the reaction mixture after the dropping, nitrogen was introduced into the liquid phase at a rate of 50 mL/min. As a result of analyzing the obtained reaction product by gas chromatography, it was confirmed that the yield of glycidol was 116.0 g, and the selectivity to glycidol was 78%. In addition, it was confirmed that after completion of the reaction, no glycerol carbonate was present in the residue.

Example 3

A 300 mL four-necked flask equipped with a fractionating column and a Liebig condenser was charged with 20.0 g (0.14 mol) of anhydrous sodium sulfate and 100.0 g of polyethylene glycol dimethyl ether (available from Merck & Co., Inc.; average molecular weight: 500), and the contents of the flask were gradually heated to 200° C. under a pressure of 6.7 kPa. Also, the temperature of the fractionating column was maintained at 100° C. Thereafter, 99.4 g (0.84 mol) of glycerol carbonate (available from Tokyo Chemical Industry Co., Ltd.) were added dropwise into the flask over 2 h. After completion of the dropping, the resulting reaction mixture was aged under a pressure of 3.3 kPa for 1 h. As a result of analyzing the obtained reaction product by gas chromatography, it was confirmed that the yield of glycidol was 44.5 g, and the selectivity to glycidol was 71%. In addition, it was confirmed that after completion of the reaction, no glycerol carbonate was present in the residue.

Example 4

A 300 mL four-necked flask equipped with a fractionating column and a Liebig condenser was charged with 20.0 g (0.14 mol) of anhydrous sodium sulfate and 20.0 g of liquid paraffin, and the contents of the flask were gradually heated to 200° C. under a pressure of 6.7 kPa. Also, the temperature of the fractionating column was maintained at 100° C. Thereafter, 100.5 g (0.85 mol) of glycerol carbonate (available from Ube Industries, Ltd.) were added dropwise into the flask over 2 h. After completion of the dropping, the resulting reaction mixture was aged under a pressure of 4.0 kPa for 1.5 h. As a result of analyzing the obtained reaction product by gas chromatography, it was confirmed that the yield of glycidol was 42.4 g, and the selectivity to glycidol was 68%. In addition, it was confirmed that after completion of the reaction, no glycerol carbonate was present in the residue.

Comparative Example 1

A 300 mL four-necked flask equipped with a fractionating column and a Liebig condenser was charged with 20.0 g (0.14 mol) of anhydrous sodium sulfate and 20.1 g (0.22 mol) of glycerol, and the contents of the flask were gradually heated to 200° C. under a pressure of 6.7 kPa. Also, the temperature of the fractionating column was maintained at 100° C. Thereafter, 100.5 g (0.85 mol) of glycerol carbonate (available from Ube Industries, Ltd.) were added dropwise into the flask over 2 h. After completion of the dropping, the resulting reaction mixture was aged under a pressure of 4.0 kPa for 1.5 h. As a result of analyzing the obtained reaction product by gas chromatography, it was confirmed that the yield of glycidol was 31.7 g, and the selectivity to glycidol was 51%. In addition, it was confirmed that after completion of the reaction, no glycerol carbonate was present in the residue.

Comparative Example 2

A 300 mL four-necked flask equipped with a Liebig condenser was charged with 23.6 g (0.17 mol) of anhydrous sodium sulfate, and the anhydrous sodium sulfate thus charged was gradually heated to 200° C. under a pressure of 6.7 kPa. Thereafter, 236.2 g (2.00 mol) of glycerol carbonate (available from Tokyo Chemical Industry Co., Ltd.) were added dropwise into the flask over 6 h. After completion of the dropping, the resulting reaction mixture was aged under a pressure of 2.7 kPa for 2 h. As a result of analyzing the obtained reaction product by gas chromatography, it was confirmed that the yield of glycidol was 31.7 g, and the selectivity to glycidol was 55%. In addition, it was confirmed that after completion of the reaction, no glycerol carbonate was present in the residue.

TABLE 1-1

| | Reaction method | Catalyst | Temperature [° C.] |
|---|---|---|---|
| Example 1 | Dropping/flowing nitrogen | Na$_2$SO$_4$ | 200 |
| Example 2 | Dropping/flowing nitrogen | Na$_2$SO$_4$ | 200 |

TABLE 1-1-continued

|  | Reaction method | Catalyst | Temperature [° C.] |
|---|---|---|---|
| Example 3 | Dropping | Na$_2$SO$_4$ | 200 |
| Example 4 | Dropping | Na$_2$SO$_4$ | 200 |
| Comparative Example 1 | Dropping | Na$_2$SO$_4$ | 200 |
| Comparative Example 2 | Dropping | Na$_2$SO$_4$ | 200 |

TABLE 1-2

|  | Pressure [kPa] | Solvent | Selectivity [%] |
|---|---|---|---|
| Example 1 | 6.7 → 2.7 | PEG* | 80 |
| Example 2 | 6.7 → 2.7 | PEG* | 78 |
| Example 3 | 6.7 → 3.3 | PEG* | 71 |
| Example 4 | 6.7 → 4.0 | Liquid paraffin | 68 |
| Comparative Example 1 | 6.7 → 4.0 | Glycerol | 51 |
| Comparative Example 2 | 6.7 → 2.7 | None | 55 |

Note *PEG: Polyethylene glycol dimethyl ether

Example 5

A reaction tube having an inner diameter of 28 mmφ and a length of 500 mmH was filled with 203 mL (167.2 g) of zeolite A3 (undersize passing through a sieve with an opening of 1.40 to 2.36 mm (8 to 12 mesh); available from Wako Pure Chemical Industries, Ltd.). Glycerol carbonate (available from Ube Industries, Ltd.) containing 75% by weight of tetraethylene glycol dimethyl ether (TEG; available from Wako Pure Chemical Industries, Ltd.) was fed to the reactor from above, and reacted at a temperature of 180° C. under a LHSV of 0.5 while flowing nitrogen at a rate of 3600 mL/min therethrough (LHSV [1/h] is the value calculated from "flow rate of liquid [mL/h]/volume of catalyst filled [mL]"). As a result of analyzing the solution obtained after the reaction by gas chromatography, it was confirmed that the conversion rate of the raw material was 36%, and the selectivity to the aimed product was 60%.

Comparative Example 3

The same procedure as in Example 5 was repeated except that glycerol carbonate (available from Ube Industries, Ltd.) solely was used as the reaction solution to be fed, thereby conducting the reaction. As a result of analyzing the solution obtained after the reaction by gas chromatography, it was confirmed that the conversion rate of the raw material was 56%, and the selectivity to the aimed product was 14%.

TABLE 2-1

|  | Reaction method | Catalyst | Temperature [° C.] |
|---|---|---|---|
| Example 5 | Fixed bed (LHSV: 0.5) | Zeolite | 180 |
| Comparative Example 3 | Fixed bed (LHSV: 0.5) | Zeolite | 180 |

TABLE 2-2

|  | Flow rate of nitrogen [mL/min] | Solvent | Selectivity [%] |
|---|---|---|---|
| Example 5 | 3600 | TEG* | 60 |
| Comparative Example 3 | 3600 | None | 14 |

Note *TEG: Tetraethylene glycol dimethyl ether

Example 6

One hundred grams of glycerol carbonate (available from Ube Industries, Ltd.), 100 g of tetraethylene glycol dimethyl ether (available from Wako Pure Chemical Industries, Ltd.) and 20 g of zeolite A3 (undersize passing through a sieve with an opening of 75 μm (200 mesh)) were mixed with each other in a 300 mL flask, and the resulting slurry solution was withdrawn from a bottom of the flask. The thus withdrawn solution was fed to a thin film type reactor having a heat-transfer area of 352 cm$^2$ equipped with an internal stirrer from above at a rate of 3.8 g/min, and reacted therein at 250° C. under normal pressures. During the reaction, nitrogen was flowed through the reactor at a rate of 1000 mL/min from below to fractionate glycidol as produced upwardly. A bottom residue of the thin film type reactor was continuously recovered to the flask and reacted again therein. After circulating the residue for 270 min, as a result of analyzing the reaction product by gas chromatography, it was confirmed that the conversion rate of the raw material was 94%, and the selectivity to the aimed product was 74%.

Comparative Example 4

The same procedure as in Example 6 was repeated except that glycerol carbonate (available from Ube Industries, Ltd.) solely was used as the reaction solution to be fed, thereby conducting the reaction. After conducting the circulation for 160 min, as a result of analyzing the reaction product by gas chromatography, it was confirmed that the conversion rate of the raw material was 80%, and the selectivity to the aimed product was 66%.

TABLE 3-1

|  | Reaction method | Catalyst | Temperature [° C.] |
|---|---|---|---|
| Example 6 | Thin film method | Zeolite | 250 |
| Comparative Example 4 | Thin film method | Zeolite | 250 |

TABLE 3-2

|  | Flow rate of nitrogen [mL/min] | Solvent | Selectivity [%] |
|---|---|---|---|
| Example 6 | 1000 | TEG* | 74 |
| Comparative Example 4 | 1000 | None | 66 |

Note *TEG: Tetraethylene glycol dimethyl ether

From the comparison between the results of Examples and Comparative Examples as shown in Tables 1 to 3 which were identical in reaction method and catalyst used to each other, it was confirmed that when conducting the decarboxylation reaction of glycerol carbonate in the presence of the solvent containing no active hydrogen as in Examples, the selectivity to the aimed reaction product was considerably enhanced as compared to that in Comparative Examples not using the solvent containing no active hydrogen.

INDUSTRIAL APPLICABILITY

According to the present invention, there is provided a process for producing glycidol from glycerol carbonate as a raw material of the glycidol with a high selectivity.

What is claimed is:

1. A process for producing glycidol, comprising the step of subjecting glycerol carbonate to decarboxylation reaction in the presence of a solvent containing no active hydrogen.

2. The process for producing glycidol according to claim 1, wherein the solvent containing no active hydrogen is an ether-based solvent and/or a hydrocarbon-based solvent.

3. The process for producing glycidol according to claim 1, wherein the solvent containing no active hydrogen is polyalkylene glycol dimethyl ether and/or liquid paraffin.

4. The process for producing glycidol according to claim 1, wherein the decarboxylation reaction is carried out in the presence of a catalyst comprising a neutral salt selected from an alkali metal salt and/or an alkali earth metal salt.

5. The process for producing glycidol according to claim 1, wherein the decarboxylation reaction is carried out using a thin film type reactor.

6. The process for producing glycidol according to claim 1, wherein the glycerol carbonate is produced by reacting glycerol with urea in the presence of an acid catalyst.

* * * * *